US012042409B2

(12) United States Patent
Rosický et al.

(10) Patent No.: US 12,042,409 B2
(45) Date of Patent: Jul. 23, 2024

(54) PROCESS OF DESIGNING AND MANUFACTURING A PROSTHETIC SOCKET

(71) Applicant: Invent Medical Group, s.r.o., Pustkovec (CZ)

(72) Inventors: Jiří Rosický, Frýdlant (CZ); Tomáš Bouma, Rychvald (CZ); Aleš Grygar, Kopřivnice (CZ)

(73) Assignee: Invent Medical Group. S.R.O., Ostrava (CZ)

( * ) Notice: Subject to any disclaimer, the term of this patent is extended or adjusted under 35 U.S.C. 154(b) by 382 days.

(21) Appl. No.: 17/635,958

(22) PCT Filed: Aug. 20, 2020

(86) PCT No.: PCT/CZ2020/050059
§ 371 (c)(1),
(2) Date: Feb. 16, 2022

(87) PCT Pub. No.: WO2021/032228
PCT Pub. Date: Feb. 25, 2021

(65) Prior Publication Data
US 2022/0339008 A1 Oct. 27, 2022

(30) Foreign Application Priority Data
Aug. 20, 2019 (CZ) .................. CZ2019-545

(51) Int. Cl.
*A61F 2/80* (2006.01)
*A61F 2/50* (2006.01)
(Continued)

(52) U.S. Cl.
CPC .............. *A61F 2/80* (2013.01); *A61F 2/5046* (2013.01); *A61F 2/76* (2013.01); *B29C 64/393* (2017.08);
(Continued)

(58) Field of Classification Search
None
See application file for complete search history.

(56) References Cited

U.S. PATENT DOCUMENTS

2018/0235779 A1* 8/2018 Dudding ............... A61F 2/7812
2019/0021880 A1* 1/2019 Herr ......................... A61F 2/60

FOREIGN PATENT DOCUMENTS

WO     2017136405 A1    8/2017
WO     WO-2017 136405 A1 *  8/2017

OTHER PUBLICATIONS

PCT International Search Report in PCT/CZ2020/050059 dated Dec. 22, 2020, 2 pages.

* cited by examiner

*Primary Examiner* — Mohammad M Ameen
(74) *Attorney, Agent, or Firm* — Servilla Whitney LLC

(57) ABSTRACT

The invention is a method of designing and manufacturing a 3D printed prosthetic socket or a standard prosthetic socket with a 3D printed distal end, comprising a step of obtaining physical data about a patient with a residual limb and a step of creating a structural design of the 3D printed prosthetic socket or standard prosthetic socket with the 3D printed distal end. The step of creating the structural design of the 3D printed prosthetic socket (3) or standard prosthetic socket with the 3D printed distal end comprises a step of determining the bulk density of the structure of the prosthetic socket between a shaped area for positioning a linking part of the liner and a distal planar area for mounting a linking adapter of the socket directly proportional to at least one of the data from a set including at least weight, patient's degree of activity, length of the residual limb, length of the prosthesis, size of the prosthetic foot, and angle between the axis of the limb and the axis of the prosthesis.

7 Claims, 23 Drawing Sheets

(51) Int. Cl.
  *A61F 2/76* (2006.01)
  *B29C 64/393* (2017.01)
  *B33Y 10/00* (2015.01)
  *B33Y 50/02* (2015.01)
  *G06F 30/17* (2020.01)
  *B29L 31/00* (2006.01)
  *G06F 113/10* (2020.01)
(52) U.S. Cl.
  CPC ............... *B33Y 10/00* (2014.12); *B33Y 50/02* (2014.12); *G06F 30/17* (2020.01); *A61F 2002/5016* (2013.01); *A61F 2002/5049* (2013.01); *A61F 2002/505* (2013.01); *A61F 2002/762* (2013.01); *B29L 2031/7532* (2013.01); *G06F 2113/10* (2020.01)

Unique identification: ☐

Input data

Upload: [3D scan] [CAD model] [Measurements]

Patient data

Amputation side: ○ Left  ● Right
Amputation level: ● TT  ○ TF  ○ Other
Weight: ☐ kg   Activity degree: ○ 1  ● 2  ○ 3  ○ 4
Distance of MPT from ground: ☐ cm   Foot size: ☐ cm
Footwear: ● Men's  ○ Women's  ○ Children's
  Heel height: ☐ cm

Residual limb

Length: ☐ cm
Flexion: ☐ °   ● Abduction:  ○ Adduction: ☐ °
Soft tissues of the limb: ● Normal  ○ Atrophied  ○ Skeletal

Fig. 2

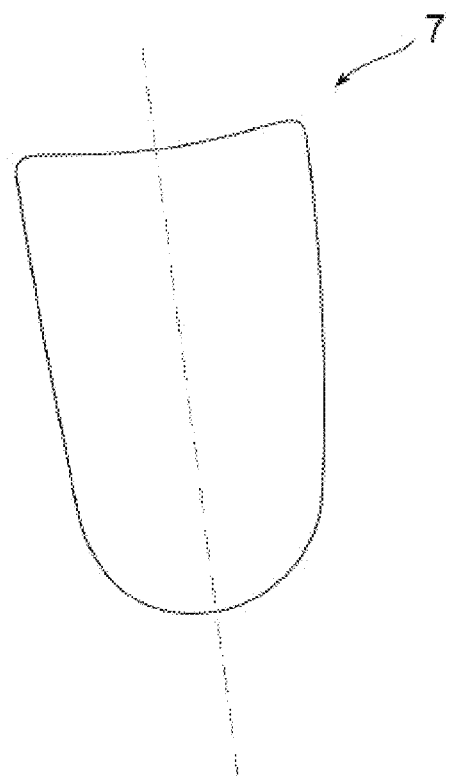
 
Fig. 3

Medial view      Frontal view
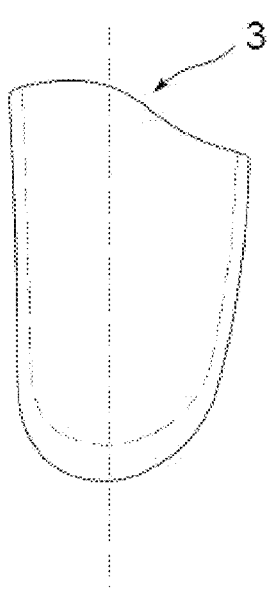 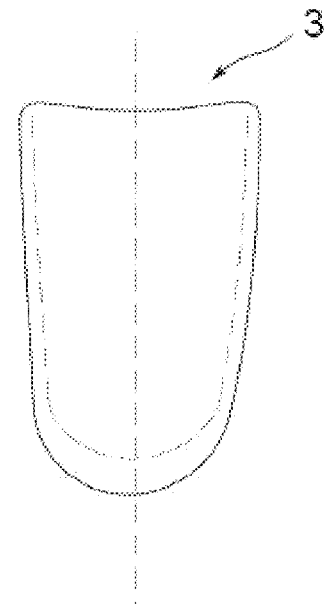
 Type 1 | Type 2 | Type 3 | Type 4 
Fig. 8

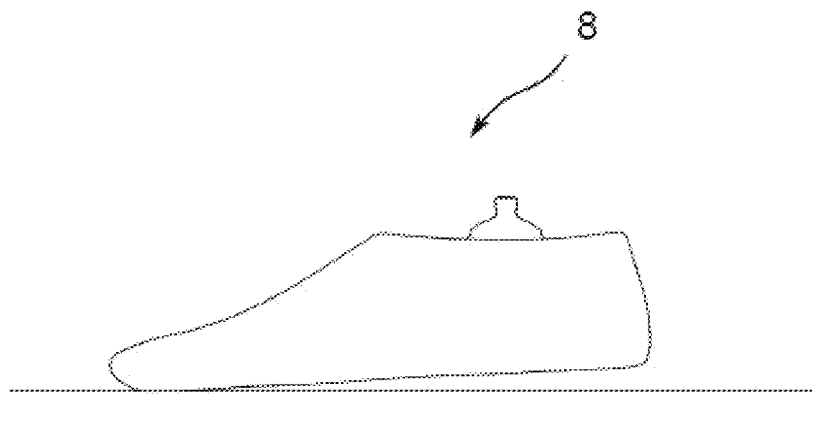

Fig. 15

Unique identification: ABC1234

Patient:

Amputation side: Right    Amputation level: TT

Weight: 88 kg    Activity degree: 2

Distance of MPT from ground: 51 cm

Foot size: 28 cm    Footwear type: men's

Heel height: 1 cm

Residual limb:

Length: 25 cm  Flexion: 5°  Abduction: 5°  Rotation: 3°

Soft tissues of the limb: Normal

Socket:

Type: TSB  Manufacture: 3D printing    Suspension: Lock

Components:

Foot:    ABC    Manufacturer: XYZ
Product no.: 12345    1 piece

Fig. 23

PROCESS OF DESIGNING AND MANUFACTURING A PROSTHETIC SOCKET

CROSS-REFERENCE TO RELATED APPLICATIONS

This application is the National Stage entry of PCT/CZ2020/050059, filed on Aug. 20, 2020 which claims priority to Czech Patent Application Number PV 2019-545, filed on Aug. 20, 2019, the disclosures of which are incorporated herein by reference in their entireties.

TECHNICAL FIELD

The invention relates to a method of designing and manufacturing a tailored 3D printed or standard prosthetic socket for a residual limb.

BACKGROUND OF THE INVENTION

High-quality and well-fitting prosthetic sockets are the basis for a comfortable life of a patient with a residual limb. Due to the individual parameters of each residual limb, it is necessary to make prosthetic sockets always tailored for the specific patient. The function of the prosthetic socket is both load-bearing, wherein weight is transferred from the residual limb to the prosthesis itself, and fixating, wherein it is necessary to ensure sufficient adhesion of the socket to the limb, but at the same time the socket need to be comfortable for the patient. Prosthetic sockets are made with respect to the physical activity of the patient and their weight. Since these parameters may change at shorter or longer intervals during the patient's life, it is desirable that the manufacture of the prosthetic socket be as simple as possible and thus less expensive.

In the current state of the art, the method of manufacturing a prosthetic socket is based on two basic steps. The first step involves obtaining the shape of the residual limb, and the second step involves making the prosthetic socket itself.

One such manufacturing method is described in the document WO2017136405, wherein the method of obtaining the shape of the residual limb consists of scanning thereof by a 3D scanner. Subsequently, a modified model is created using a software, the shape and size of which are based on the scanned residual limb. This model may be further altered, and based on its final form, a corresponding prosthetic socket is selected from the database, the structural data of which are sent to a 3D printer. The prosthetic socket itself is manufactured from the distal end, wherein when the space for the connecting adapter is created, printing is paused, the connecting adapter is manually inserted into the space, and then printing is resumed. The subsequent spatial arrangement of the prosthetic socket and prosthetic parts is performed completely manually. A disadvantage of this solution is the intermittent printing of the prosthetic socket, which can weaken the joints. Another disadvantage is the subsequent manual spatial arrangement of the prosthetic socket and prosthetic parts.

In the patent document U.S. Pat. No. 9,480,581, a method of manufacturing the prosthetic socket is described, wherein the method of obtaining the shape of the residual limb consists of scanning thereof by a 3D scanner. Subsequently, a modified model is created using a software, the shape and size of which are based on the scanned residual limb. This model may be further altered, and based on its final form, a test plastic prosthetic socket is made. Subsequently, the spatial arrangement of the test prosthetic socket and prosthetic parts is manually created. This final spatial arrangement is scanned using the 3D scanner and converted to a digital form. Based on the modified model and the final spatial arrangement, the final prosthetic socket is printed using a 3D printer. A disadvantage lies in the more expensive manufacture and use of excessive amounts of material during the manufacture. Another disadvantage of this solution is the manual spatial arrangement of the prosthetic socket and prosthetic parts.

Another possible solution, which is described in the document WO2017151577, is a method of obtaining the shape of the residual limb using a 3D scanner. The scanned data are converted to a modified model using a software, the shape and size of which are based on the scanned residual limb. This model may be further altered, and based on its final form, an inner and outer prosthetic socket is printed using a 3D printer. A disadvantage of this solution is the manual spatial arrangement of the prosthetic socket and the prosthetic parts.

Another possible solution, which is described in the document U.S. Pat. No. 9,636,238, is a method of obtaining the shape of the residual limb using scanning devices, such as a laser. Subsequently, a modified model is created using a software, the shape and dimensions of which match the scanned residual limb. Based on the modified model, the desired shape of the socket is determined. Subsequently, the model of the socket is made on a CNC machine. Then the inner side of the created prosthetic socket is scanned, and a surface model is created using a software. Reference points are selected on the modified model and surface model, and possible deviations between them are then calculated. If these deviations differ by more than the selected threshold, the shape and size of the final prosthetic socket are changed. A disadvantage of this solution is the need to recalculate the deviations between the reference points. Another disadvantage of this solution is the manual spatial arrangement of the prosthetic socket and prosthetic parts.

For the above-mentioned reasons, it would be desirable to come up with a solution that would allow the virtual spatial arrangement of the prosthetic socket and the prosthetic parts. The advantage would be mainly in saving time and using materials efficiently.

SUMMARY OF THE INVENTION

The above shortcomings are eliminated to a certain extent by a process of designing and manufacturing a 3D printed prosthetic socket or a standard socket with a 3D printed distal end including five sub-steps. The first step is to obtain the physical data about the patient with a residual limb, including at least one physical datum from a set comprising at least weight, degree of activity, geometry of the axis of the residual limb, dimensional parameters of the residual limb, and dimensional parameters of the other limb. The second step is to obtain or create a digital representation of the modified area of the residual limb. The third step is to create the structural design of 3D printed or standard prosthetic socket with 3D printed distal end based on the obtained physical data about the patient, and/or based on the digital representation of the modified area of the residual limb. The fourth step is to send the structural design data of the prosthetic socket or 3D printed distal end of the standard socket to a 3D printer. The fifth step is to make the prosthetic socket by means of 3D printing or in a standard manner, i.e. by lamination, thermoplastic shaping using the 3D printed distal end of the socket. Creating the structural design of the 3D printed or standard prosthetic socket with the 3D printed distal end comprises determining the bulk density of the structure of the prosthetic socket between a shaped area for positioning a linking part of the liner and a distal planar area for mounting a linking adapter of the socket directly proportional to at least one of the data from a set including at least weight, degree of activity of the patient, length of the residual limb, length of the prosthesis, size of the prosthetic foot, and angle between the axis of the limb and the axis of the prosthesis. Since the distal end forms a significant portion of the volume of the socket, by optimising the lightened structure, the weight of the entire socket is reduced and thereby the comfort of the patient with the residual limb is increased and material is saved.

In a preferred embodiment, obtaining the physical data about the patient with the residual limb comprises a step of measuring the circumference of the residual limb in at least two anticoincident planes perpendicular to the axis of the limb, and their mutual distance, and their distance from a reference anatomical point of the residual limb.

In a preferred embodiment, the step of obtaining the digital representation of the modified area of the residual limb comprises a step of making a physical model of the residual limb, a step of modifying the outer area of the physical model of the residual limb, and a step of digitising the outer area of the modified physical model of the residual limb.

In a preferred embodiment, the step of obtaining the digital representation of the modified area of the residual limb comprises a step of digitising the inner area of the existing prosthetic socket, or a step of making the physical model of the residual limb from the existing prosthetic socket, and a step of digitising the outer area of the modified physical model of the residual limb.

In a preferred embodiment, the step of obtaining the digital representation of the modified area of the residual limb comprises a step of altering the area of the scan of the residual limb, or the area of its exact casting, on a computer using a software.

In a preferred embodiment, the step of obtaining the digital representation of the modified area of the residual limb comprises a step of altering the computer model of the residual limb designed using the obtained measurements on a computer using a software.

In a preferred embodiment, the step of obtaining the digital representation of the modified area of the residual limb includes transforming the obtained data into a polygonal network of definition points of a density of at least 10 points per cm2.

In a preferred embodiment, the structural design of the prosthetic socket comprises a step of obtaining a digital representation of the area of the healthy limb and a step of spatially arranging the digital representation of the area of the healthy limb relative to the digital representation of the modified area of the residual limb based on the axis of the limb and the axis of the prosthesis.

DESCRIPTION OF DRAWINGS

Summary of the invention is further clarified using exemplary embodiments thereof, which are described with reference to the accompanying drawings, in which:

FIG. 2 shows the input data required for the design of the 3D printed prosthetic socket or the standard prosthetic socket with the 3D printed distal end, FIG. 3 shows the digital surface of the residual limb, FIG. 8 shows selection of the prosthetic socket type, FIG. 15 shows selection of the type of the foot, FIG. 23 shows resulting summary of the prosthesis design information.

EXEMPLARY EMBODIMENTS OF THE INVENTION

Figure 1:
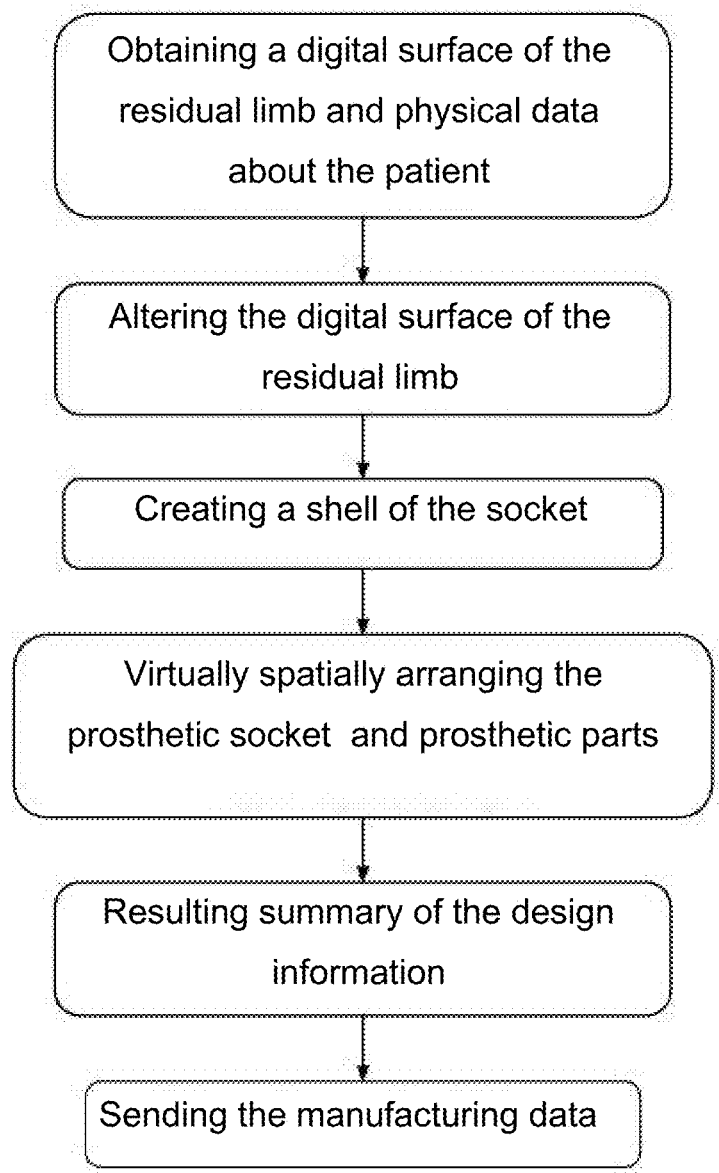
FIG. 1 shows a flow chart of the process of designing and manufacturing a 3D printed or a standard prosthetic socket with a 3D printed distal end according to the invention.

Said embodiments describe only exemplary variants of the embodiments of the invention, and the invention defined in the claims can be realised in a number of other specific embodiments, which are not described below.

A method of manufacturing a 3D printed or a standard prosthetic socket 3 with a 3D printed distal end of the present invention is implemented using a system of communicatively interconnected scanner, computer device and 3D printer. The computer device contains in its memory a software application, which comprises a database of prosthetic parts and an interactive configurator, which comprises a patient data collection module, a module for determining the virtual spatial arrangement of the prosthesis 6, a module for displaying mutual location of the prosthetic socket 3 and the prosthetic foot 8, a module for selecting the corresponding prosthetic parts, and a module for data export. In an alternative embodiment, the interactive configurator further comprises a database of basic samples of the prosthetics socket 3. In another embodiment, the interactive configurator further comprises a system for designing the prosthetic socket 3. In another exemplary embodiment, the computer device does not contain the database of basic samples of the prosthetic socket 3, instead, it contains the system for designing the structure of the prosthetic socket 3 based on the modified area of the residual limb on a computer, manually or using an automatic or semiautomatic algorithm. In another exemplary embodiment, the computer device contains a web browser for connecting to a web or cloud application that comprises the database of prosthetic parts, the database of basic samples of the prosthetic socket 3, and, furthermore, the interactive configurator that comprises the patient data collection module, the module for determining the virtual spatial arrangement of the prosthesis 6, and the module for data export. In another exemplary embodiment, the computer device contains a web browser for connecting to a web or cloud application that does not contain the database of basic samples of the prosthetic socket 3, instead, it contains the system for designing the structure of the prosthetic socket 3 based on the modified area of the residual limb on a computer, manually or using an automatic or semiautomatic algorithm.

The control device on which such an application is installed can be any suitable hardware. This includes, for example, PC, MAC, virtual reality (VR), augmented reality (AR), laptops, tablets, and other mobile devices that are commonly used nowadays. Such devices use various operating systems for which the given application is always adapted so that it is possible to control it on the given device and use all user inputs that the device allows. The communication connection of the individual devices of the above described system is implemented using wires, for example, using ethernet, USB, thunderbolt, or another suitable communication means, or, alternatively, the communication connection is implemented wirelessly, using for example, Wi-Fi, Bluetooth, GSM, LTE, and other suitable wireless connection systems.

The method of manufacturing the 3D printed or standard prosthetic socket 3 with the 3D printed distal end according to the flow chart of FIG. 1 includes obtaining a digital surface 7 of the residual limb and information about the patient, possibly altering the digital surface 7 of the residual limb, creating a shell of the prosthetic socket 3 comprising the altered digital surface of the residual limb, virtually spatially arranging the prosthetic socket 3 and prosthetic parts, and the resulting summary of the design information, and sending the manufacturing data. The prosthetic parts include a linking adapter of the socket 4; connecting adapters; tube adapters 9; prosthetic foot 8, namely standard, dynamic, bionic; prosthetic ankle joint; prosthetic knee joint 11; linking parts 10, namely lock, valve, string.

The step of obtaining the digital surface 7 of the residual limb, which is shown in FIG. 3, is, in the first exemplary embodiment, implemented using a 3D scanner that converts the surface of the limb to a geometric model of a polygonal network, wherein the density of the network points is at least ten points per $cm^2$. To obtain these points, many different technologies are used, namely optical scanners, cameras, x-ray devices, magnetic tomographs, lasers, touch sensors. After the technologies used, the individual methods of scanning are named, i.e., for example, x-ray, ultrasound, laser, optical, or mechanical 3D scanners. Alternatively, the digital surface 7 of the residual limb may be obtained by measuring the circumferences of the residual limb in at least two anticoincident planes perpendicular to the axis of the limb, and their mutual distance, and the distance of a reference anatomical point 1 of the residual limb. Preferably, the digital surface 7 of the residual limb may be obtained by measuring the circumferences of the residual limb in at least two anticoincident planes perpendicular to the axis of the limb, and their mutual distance, and the distance of the reference anatomical point 1 of the residual limb, and, simultaneously, by 2D photographs of the limb from the front and the side in order to determine the spatial orientation of the residual limb. In another exemplary embodiment, the spatial orientation of the residual limb may be obtained by directly measuring the axis of the limb using a goniometer. In another exemplary embodiment, the digital surface 7 of the residual limb may be obtained using MRI or CT. The scanned or measured residual limb comprises a liner. The liner is a sleeve for the residual limb that separates the skin from the hard limb socket, protects the residual limb from abrasion, and also includes a linking part 10. Alternatively, the residual limb may be scanned or measured also without the liner. Subsequently, the digital surface 7 of the residual limb is converted to a software application of the computer device, wherein the digital surface 7 representing the surface of the residual limb is obtained. The digital surface 7 of the residual limb maintains the shape and volume of the residual limb, and after modifying the digital surface 7, it is the basic shape of the prosthetic socket 3, which is altered in the subsequent steps using the software application. In another exemplary embodiment, obtaining the digital representation of the modified area of the residual limb comprises a step of making a physical model of the residual limb, a step of manually modifying the outer area of the physical model of the residual limb, and a step of digitising the outer area of the modified physical model of the residual limb using the above-mentioned scanning methods. The modified model obtained in this manner is not subsequently altered using the software application, and it is the basic shape of the prosthetic socket 3. In this step, a digital representation of the area of the healthy limb is also obtained. In another exemplary embodiment, obtaining the digital representation of the modified area of the residual limb comprises a step of digitising the inner area of the existing prosthetic socket 3, or a step of creating a physical model, the shape of which corresponds to the inner area of the existing prosthetic socket 3, and a step of digitising the physical model using the above-mentioned scanning methods. The modified model obtained in this manner is not subsequently altered using the software application, and it is the basic shape of the prosthetic socket 3.

The step of obtaining patient physical data with an amputation below the knee includes obtaining input data, i.e. the amputation side, namely left, right; weight; degree of activity, namely low, medium, high, very high; size of the foot; type of footwear, namely women's, men's, children's; and, furthermore, the dimensional parameters of the residual limb, namely length, flexion, abduction or adduction, outer and inner rotation; type of the limb, namely muscular, normal, atrophied, skeletal; distance of the centre of the patellar ligament (MPT) from the ground. The step of obtaining patient physical data with an amputation above the knee includes obtaining input data, i.e. the amputation side, namely left, right; weight; degree of activity, namely low, medium, high, very high; size of the foot; type of footwear, namely women's, men's, children's; and, furthermore, the dimensional parameters of the residual limb, namely length, flexion, abduction or adduction, outer and inner rotation; type of the limb, namely muscular, normal, atrophied, skeletal; distance of the ischium from the ground; distance of the centre of the knee joint of the non-amputated limb from the ground. The user interfaces of the application for inputting all the input data needed to design the 3D printed or standard prosthetic socket 3 with the 3D printed distal end are shown in FIG. 2.

Figure 4:
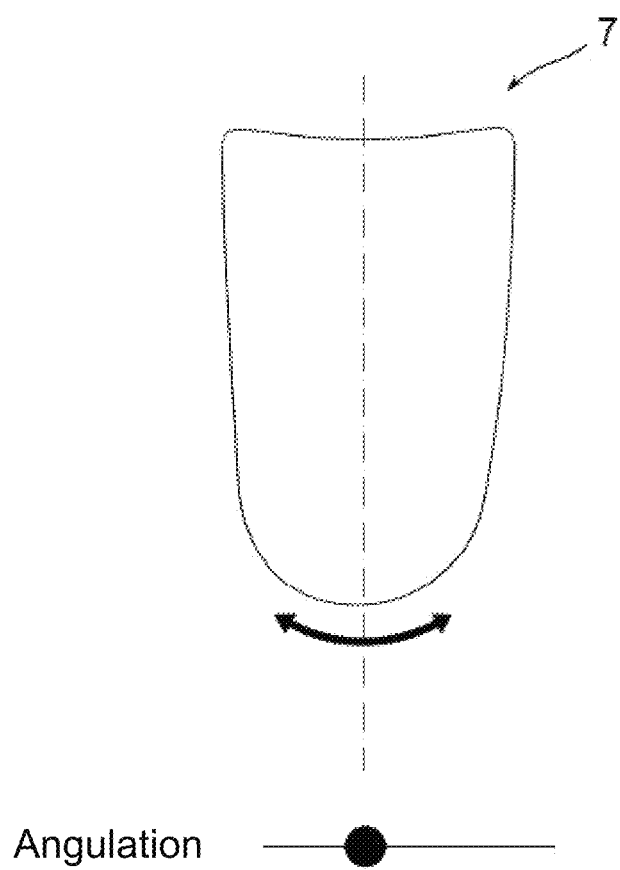
FIG. 4 shows alignment of the digital surface of the residual limb.
Figure 5:
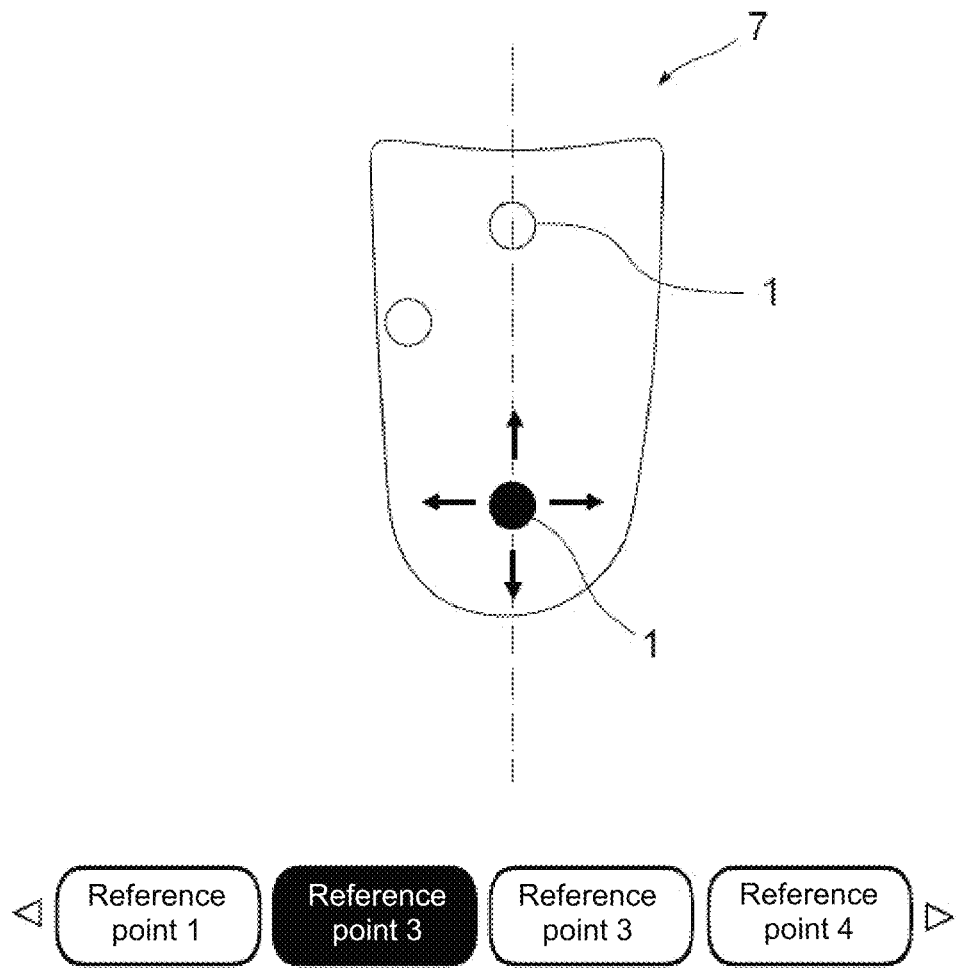
FIG. 5 shows alteration of reference points.
Figure 6:
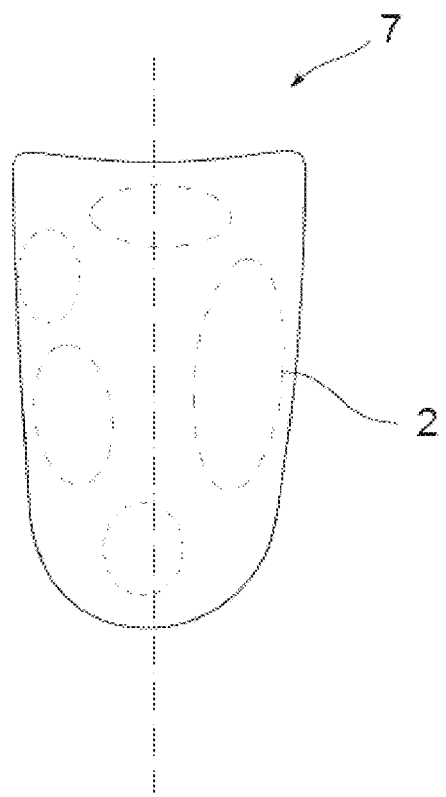
FIG. 6 shows automatic modification.
Figure 7:
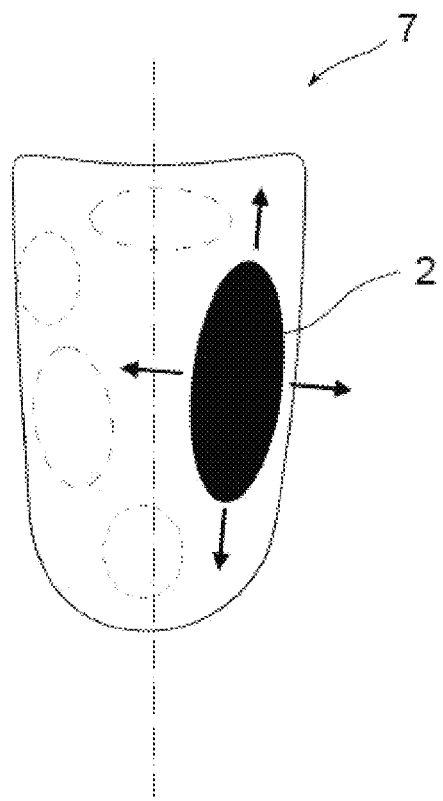
FIG. 7 shows manual modification.

The step of altering the digital surface 7 shown using the computer device comprises, on the one hand, smoothing the digital surface 7 of the residual limb, then decreasing or increasing the length of the digital surface 7 of the residual limb, and also changing its angulation, which is shown in FIG. 4. As is apparent from FIG. 5, as part of the alteration of the digital surface 7 of the residual limb, reference points 1 which indicate the location of the soft tissues and bones within the residual limb are automatically or manually selected. These reference points 1 are, in the case of an amputation below the knee, located, for example, in the centre of the patellar ligament, fibula head, tibia and fibula ends, proximal edge of condyles or posterior clipping edge. In case of an amputation above the knee, these reference points 1 are located, for example, on the ischium, end of femur, trochanter, Scarp triangle, below the gluteal sulcus. Based on these reference points 1, zones 2 of various sizes are created, and the measuring planes are selected. In an exemplary embodiment, the planes are perpendicular to the axis of the limb, and, furthermore, in case of an amputation below the knee, they relate to the distal end of the limb or the centre of the patellar ligament, in case of an amputation above the knee, the distal end of the limb or the ischium. After the suitable plane is selected, a measurement table is created. This table contains the sizes of the circumferences in the given plane and, furthermore, the spacings in the sagittal and frontal plane, or diagonal spacings. Based on the reference points 1 and the created zones 2, an automatic modification, which is shown in FIG. 6, or a manual modification, which is shown in FIG. 7, is subsequently performed. Both modifications include selecting the type of the prosthetic socket 3 from the database, which is shown in FIG. 8. In an exemplary embodiment, in case of an amputation below the knee, a TSB prosthetic socket 3 may be selected, where the label TSB of the prosthetic socket 3 is an abbreviation of the descriptive label Total Surface Bearing (load transfer over the entire area of the prosthetic socket 3). In case of the TSB prosthetic socket 3, the load is distributed over the entire surface of the residual limb. The structure is based on the presumption that even pressure-sensitive regions may withstand a certain load. A condition for making the TSB prosthetic socket 3 is the use of an inner viscoelastic limb socket, which helps to distribute the forces acting on the sensitive regions of the limb and, furthermore, solves the suspension of the prosthesis 6 in the swing phase. The TSB prosthetic socket 3 has a shape and volume that are very similar to the residual limb. The lightening of the sensitive regions is implemented by means of a viscoelastic prosthetic socket 3 or viscoelastic pellets integrated into the supporting prosthetic socket 3 of the prosthesis 6. In another exemplary embodiment, a PTB prosthetic socket 3 may be selected, where the label PTB of the prosthetic socket 3 is an abbreviation of the descriptive label Patellar Tendon Bearing (load transfer over the patellar ligament). When the PTB prosthetic socket 3 is used, especially regions tolerating higher pressures well are loaded. The loadable portions of the limb are used for load transfer, for control of the rotation of the limb in the socket (triangular cross-section of the socket), for antero-posterior and medio-lateral stability of the limb. On the other hand, the sensitive regions of tran-stibial limb are lightened. The suspension of the PTB prosthetic socket 3 is solved by a suprapatellar strap. In an alternative embodiment, a KBM prosthetic socket 3 may be selected, where the label KBM of the prosthetic socket 3 is an abbreviation of the German label Kondylen Bettung Münster (after the anatomical shape and place of origin). The KBM prosthetic socket 3 is a modification of the PTB prosthetic socket 3. The shape is changed at the proximal end. The prosthetic socket 3 medially and laterally copies the shape of the condyles, and this skeletal suspension over the condyles of the femur is preferably used in the swing phase. The KBM prosthetic socket 3 is sometimes also referred to as a PTB-SC (supracondylar) prosthetic socket 3. In an exemplary embodiment, in case of an amputation above the knee, a limb socket with support on the ischium may be selected (load transfer mainly over the skeleton of the pelvis) or a prosthetic socket 3 with the ischium buried (load transfer mainly over the soft tissues of the limb). The prosthetic socket 3 with the ischium buried is referred to as an IC prosthetic socket 3, after the English name Ischial Containment. Furthermore, this step allows to either automatically or interactively modify the area of the limb for the above selected type of the prosthetic socket 3. In an exemplary embodiment of the automatic modification, automatic alteration of the created zones 2 is performed according to the default values. In an alternative embodiment of the interactive modification, the user can alter the zones 2 individually. The alteration of the zones 2 allows the volume or circumference of the zone 2 to be reduced, the position of the zone 2 to be changed. In case of an amputation below the knee, the alteration of the zones 2 means lowering the regions in the centre of the patellar ligament in a gradient manner inwards to the model of the residual limb, lowering the regions medially or laterally from the tibia in a gradient manner inwards to the model of the residual limb, lowering the region in a posterior or supracondylar gradient manner inwards to the model of the residual limb, elevating the region of the fibula head in a gradient manner outwards from the model of the residual limb, elevating the tibia region in a gradient manner outwards from the model of the residual limb, and elevating the posterior region above the edge of the prosthetic socket 3 in a gradient manner outwards from the model of the residual limb. In case of an amputation above the knee, the alteration of the zones 2 means lowering the region longitudinally around the femur flat inwards to the model of the residual limb, lowering the region semi-arcuately above the trochanter in a gradient manner inwards to the model of the residual limb, elevating the region of the inner adductors in a gradient manner outwards from the model of the residual limb, lowering the region semi-arcuately behind the trochanter in a gradient manner inwards to the model of the residual limb. As is shown in FIG. 6, for the selected type of modification, default zones 2 and their sizes are determined, i.e. a curve on the surface of the limb 7, which delimits the zone 2. Furthermore, the default values include the size of the gradient change of the zone 2 inwards to or outwards from the model of the residual limb. The default values of the location of the zone 2 are based on the anatomical points 1. In an exemplary embodiment, in the case of an amputation below the knee, in order to lighten the fibula head, the zone 2 has a circular shape, its centre is located in the reference anatomical point 1 of the fibula head, and the modification is in a gradient manner outwards from the model of the residual limb. In case of a residual limb with normal soft tissues, the diameter of the zone 2 is 3-5 cm, and the apex of the modified area is 3-5 mm away from the model of the residual limb. These default values are shown in the table, depending on the dimensions of the limb and the condition of the soft tissues of the limb. The user may change the default values themselves in accordance with the patient's individual needs. After the automatic or interactive modification, a modified digital surface 7 of the residual limb is created. Furthermore, the software application creates a structural design of the 3D printed or standard prosthetic socket 3 with the 3D printed distal end based on the modified digital surface 7 of the residual limb, information about the patient, dimensional parameters of the residual limb, and the spatial position of the modular parts of the prosthetic socket 3. In one of the exemplary embodiments, the TSB prosthetic socket 3 type is selected in the software application, and, based on the modified area of the socket and the linking adapter of the socket 4, a shell of the prosthetic socket 3 is created, wherein the width of the wall of the prosthetic socket 3 is generated based on the weight, activity, length of the limb, prosthesis 6, and prosthetic foot 8, and may take values within the range of about 1-10 mm. The elastic regions in the socket 3 are positioned in the shell in order to lighten the residual limb based on the location of the reference points 1, and their size is determined by the dimensions of the limb. According to the selected linking part 10, a spatial recess is generated in the shell for positioning the linking part 10. The upper curve of the prosthetic socket 3 extends medially and laterally in the upper half of the condyles of the femur, anteriorly at a height of 1-3 cm from the centre of the patellar ligament, posteriorly below the insertions of the medial and lateral hamstring.

The step of creating the shell of the prosthetic socket 3 comprises the creation of the structural design of the 3D printed or standard prosthetic socket 3 with the 3D printed distal end based on the modified digital surface 7 of the residual limb, information about the patient, dimensional parameters of the residual limb, and spatial position of the modular parts of the prosthetic socket 3. This step also includes automatically determining the bulk density of the structure of the distal end of the 3D printed or standard prosthetic socket 3 with the 3D printed distal end that, in a directly proportional manner, depends on at least one of data from a set including at least weight, patient's degree of activity, length of the residual limb, length of the prosthesis 6, size of the prosthetic foot 8, and angle between the axis of the limb and the axis of the prosthesis 6. In one exemplary embodiment, there is a database of distal end structures with different bulk densities. After inputting the input parameters that are defined, for example, as follows: weight of 88 kg, degree of activity of 2, length of the transtibial prosthesis 6 of 51 cm, size of the foot 8 of 28 cm, length of the limb of 25 cm, flexion of the limb of 5 degrees, adduction of the limb of 5 degrees, a structure with a bulk density that best matches the inputted parameters is selected from the database based on a combination of the selected parameters. The structures for the distal end with different bulk densities are added to the database for the selected combinations of the input parameters, wherein the structural arrangement of these structures is optimised using the finite element method. This so-called topological optimisation ensures the most suitable arrangement and density of the reinforcements, or the whole structure of the prosthetic socket 3, such that the distal end meets the strength requirements and, simultaneously, as little material as possible is used, i.e. such that the bulk density is as small as possible and thus the weight of the entire distal end is as low as possible. The calculation algorithm for determining the bulk density of the structure of the distal end of the 3D printed or standard prosthetic socket 3 with the 3D printed distal end of the prosthesis 6 is based on a geometric model of the prosthesis 6, material properties of the materials used, and load on the prosthesis 6. The basic geometric parameters of the prosthesis 6 determine the spatial conditions for the calculation algorithm, which is governed by the international standard ČSN EN ISO 10328 (844004). While walking, the prosthesis 6 is loaded by a cyclic combined load, i.e. bending, pressure, torsion. The tests described in this international standard include static and cyclic tests, wherein the calculation algorithm is based on 2 critical loading conditions, i.e. load on the heel when walking and load on the tip of the foot 8 when walking. The standard specifies the edge geometric and loading forces for performing the tests. In a preferred embodiment, the distal end of the prosthetic socket 3 is composed of a distal planar area, on which openings for mounting the adapters 4 are positioned, and proximally of the shaped area for positioning the linking part 10. The outer shape of the distal end is composed of spatially curved areas, which are based on the commonly used shape of the prosthetic socket 3. The shape-complex geometry of the distal end of the prosthetic socket 3 must be discretised with the help of controlled generation of, for example, tetrahedral finite elements or reinforcing ribs, which ensure higher accuracy of the embodiment of the distal end. The profile, shape and width of the tetrahedral finite elements or reinforcing ribs changes based on the selected parameters, i.e. the higher the weight, or the higher the degree of activity, the thicker their dimensions, the higher their density of representation, or a combination of these occurs. Alternatively, the inner structure of the distal end may be generated from any multihedral elements or monohedral elements, of a circular or elliptical cross-section.

Figure 9:
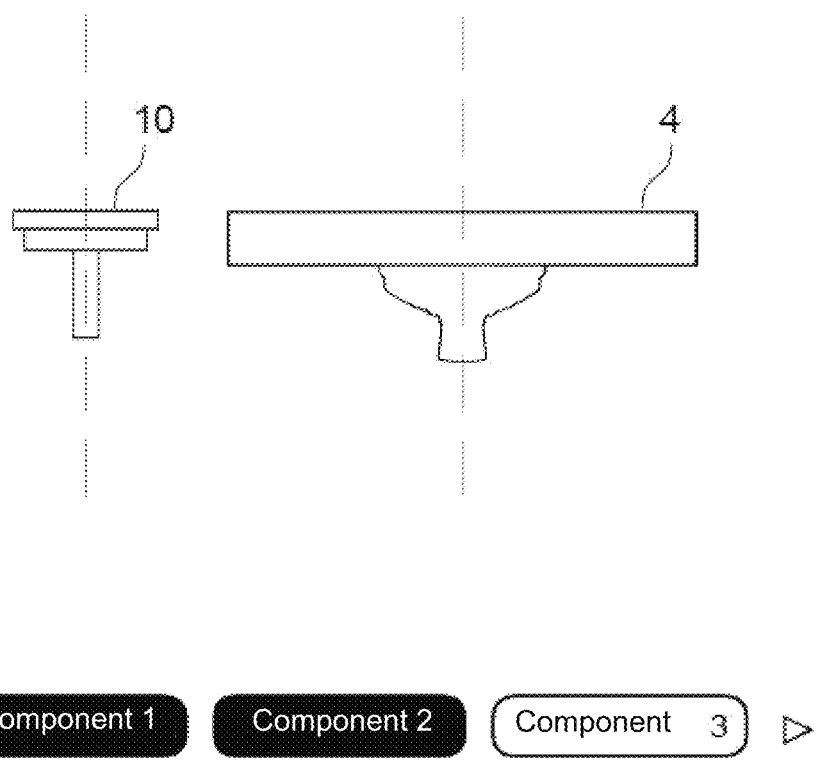
FIG. 9 shows selection of the prosthetic parts.
Figure 10:
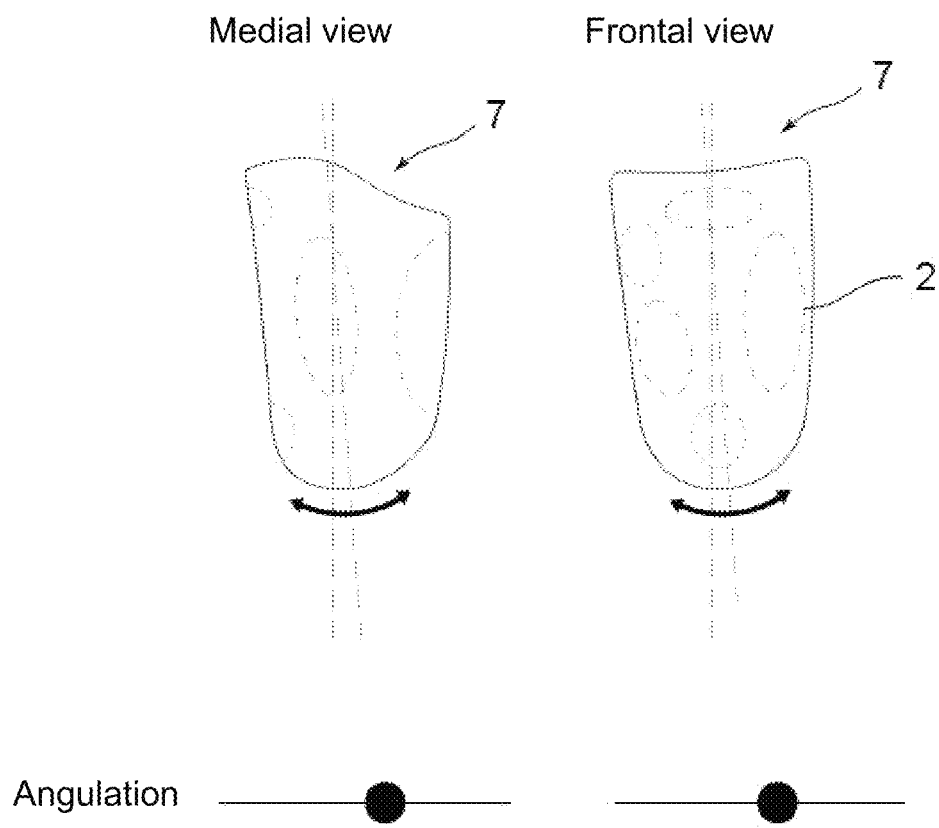
FIG. 10 shows alignment of the residual limb.
Figure 11:
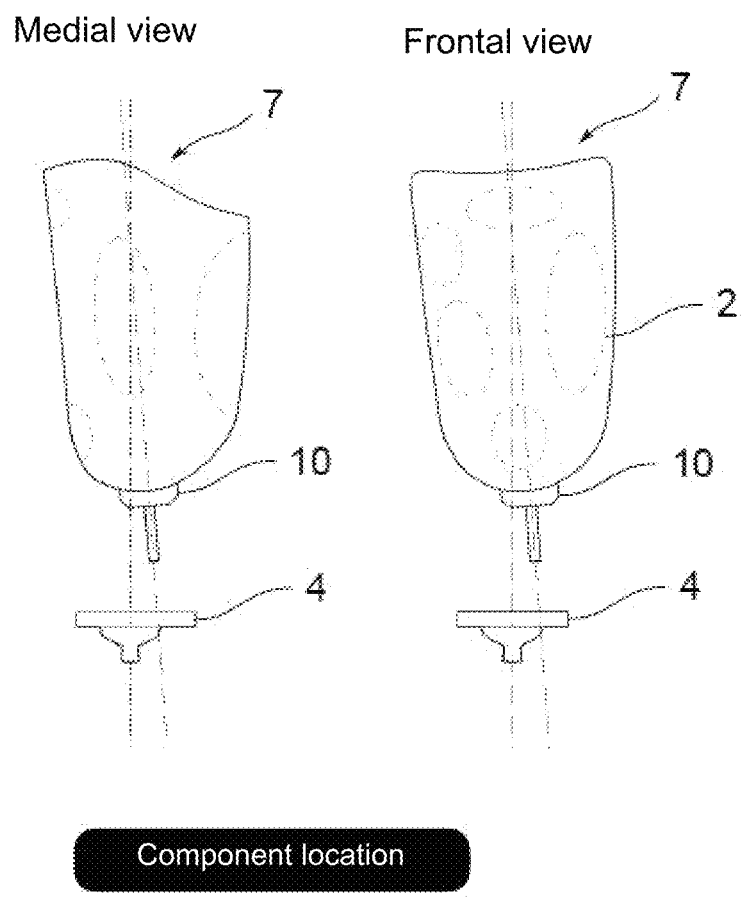
FIG. 11 shows the position of the selected prosthetic parts.
Figure 12:
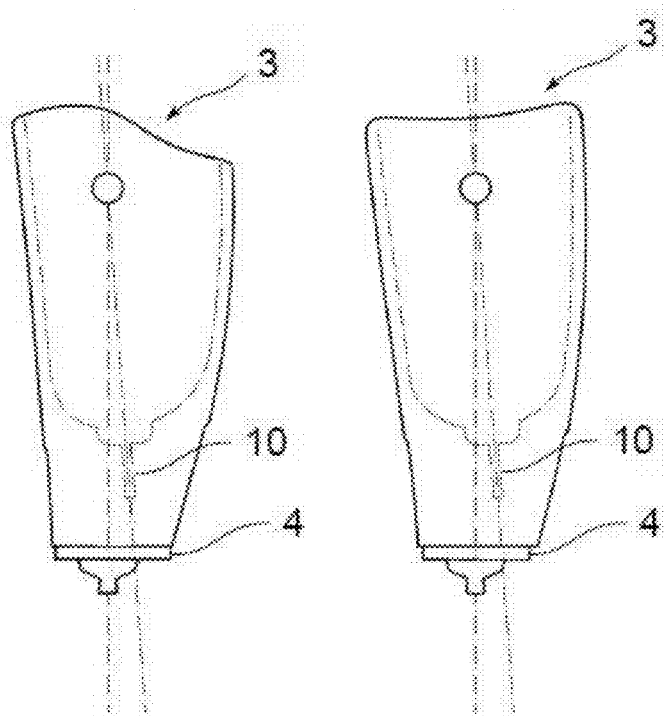
FIG. 12 shows an automatically designed prosthetic socket.
Figure 13:
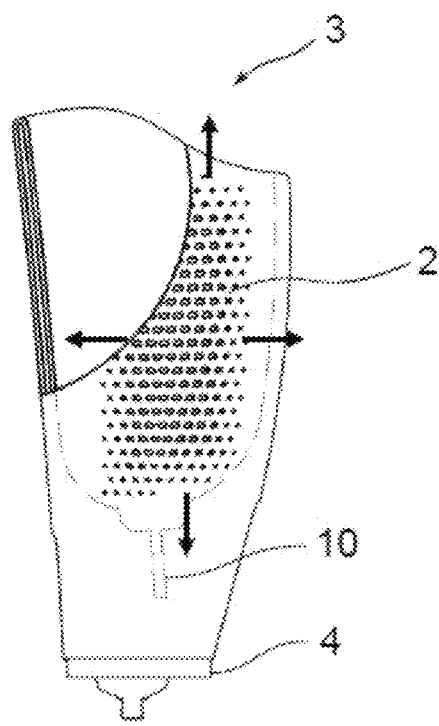
FIG. 13 shows modification of selected zones of the 3D printed socket.
Figure 14:
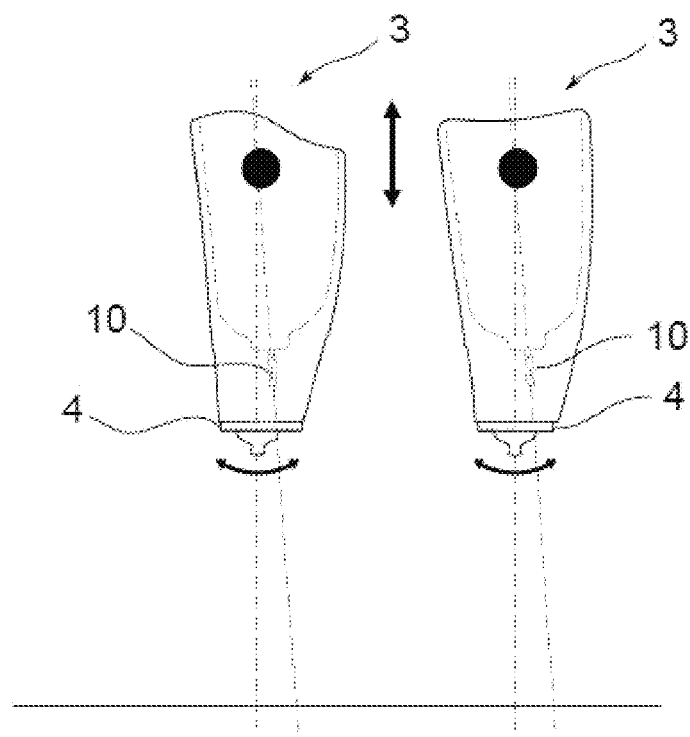
FIG. 14 shows manual alignment of the prosthetic socket with the prosthetic parts positioned.
Figure 16:
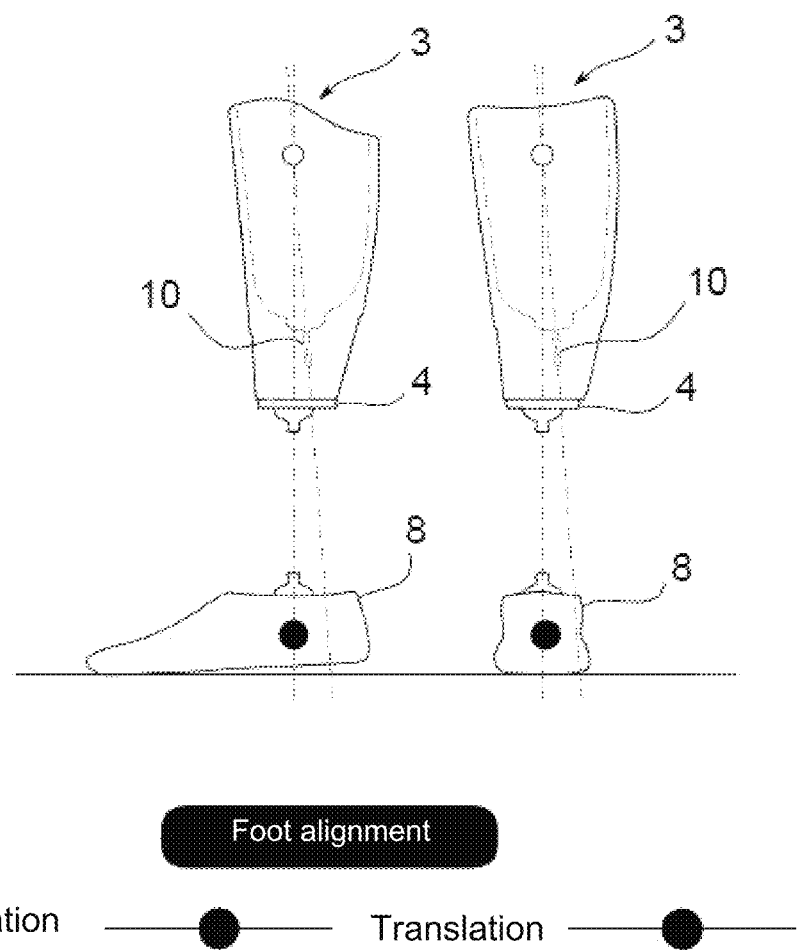
FIG. 16 shows manual alignment of the prosthetic foot.
Figure 17:
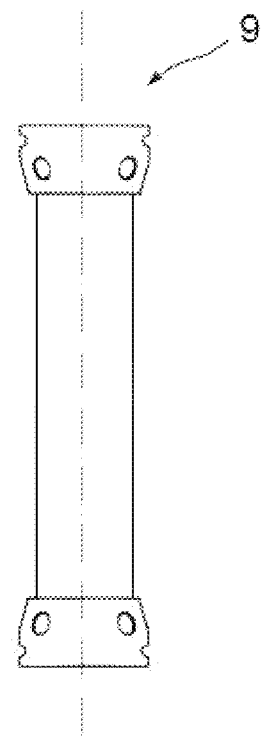
FIG. 17 shows selection of the prosthetic parts.
Figure 18:
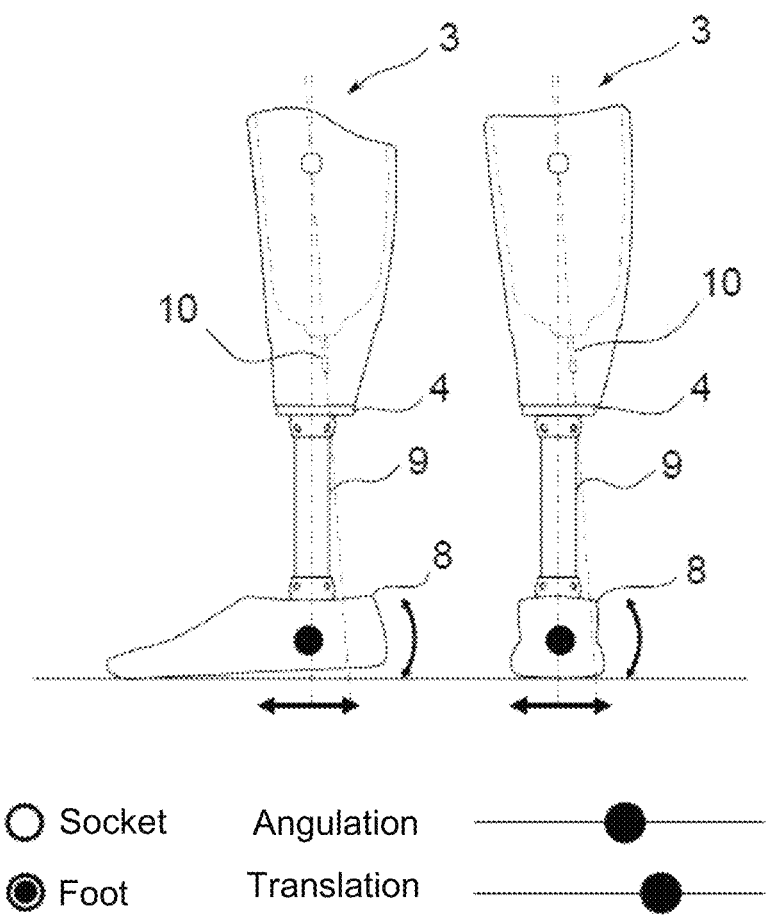
FIG. 18 shows manual alignment of the prosthetic socket, prosthetic parts, and foot.
Figure 19:
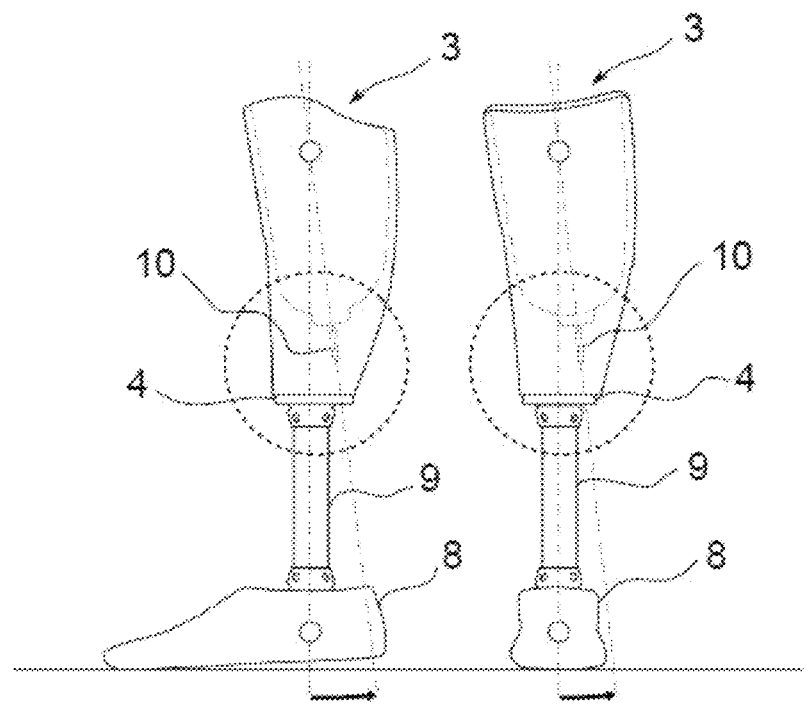
FIG. 19 shows modification of the prosthetic socket.
Figure 20:
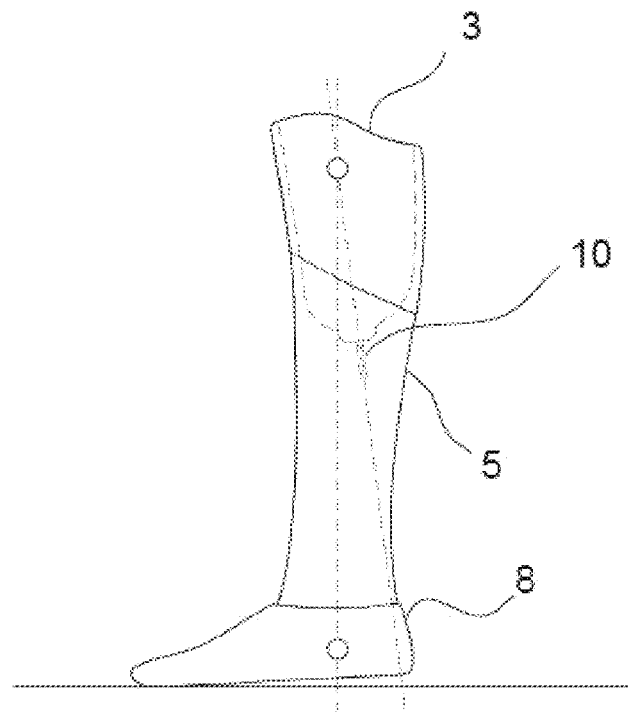
FIG. 20 shows selection of the cover of the prosthetic socket.
Figure 21:
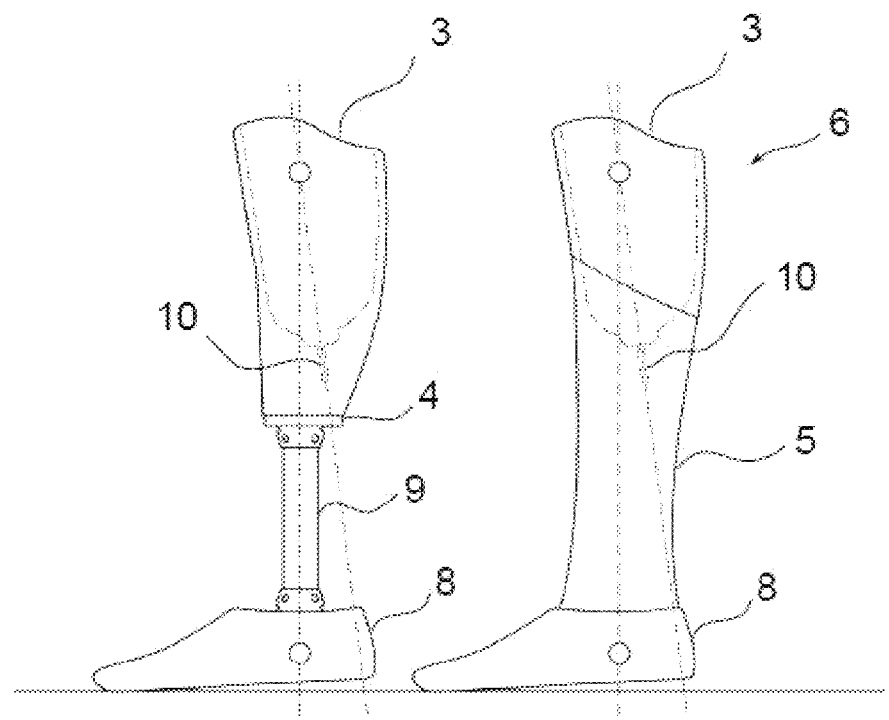
FIG. 21 shows a final design of a transtibial prosthesis.
Figure 22:
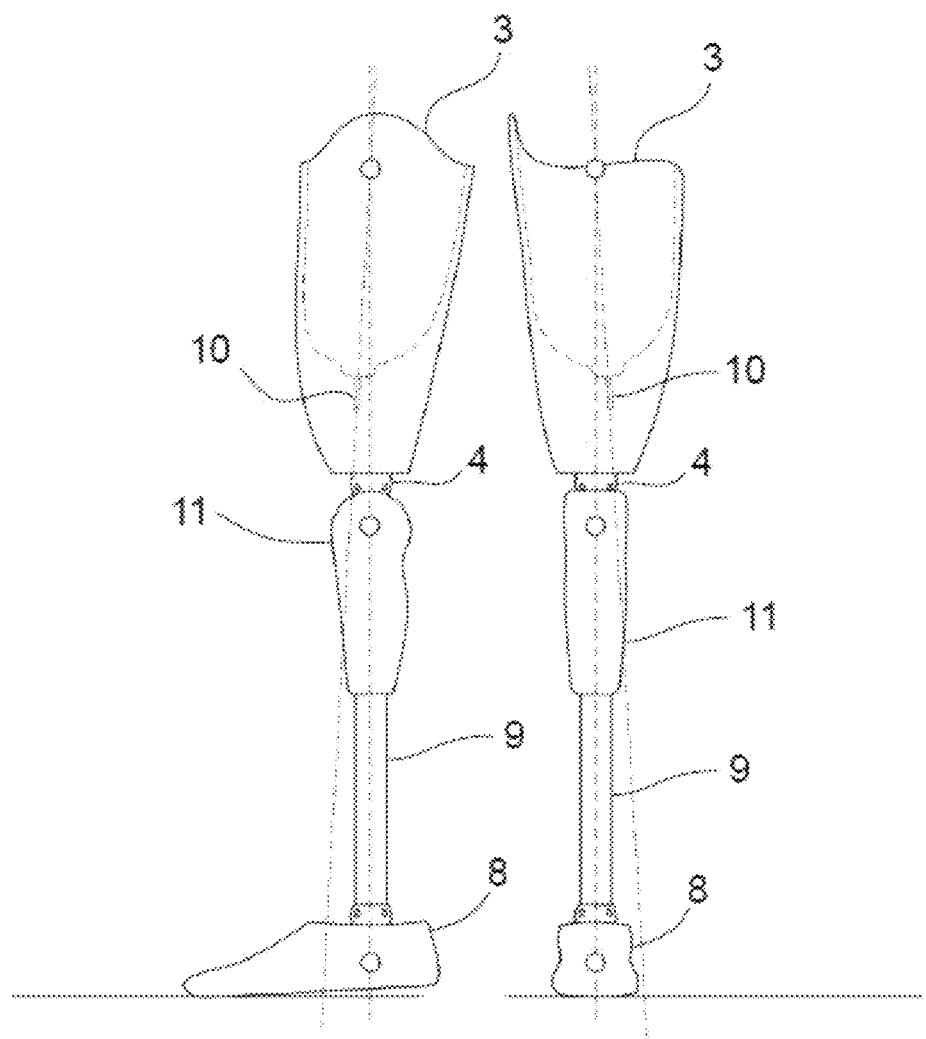
FIG. 22 shows a design of a transfemoral prosthesis.

In another exemplary embodiment of the step of creating the shell of the prosthetic socket 3, a step of automatically determining the bulk density of the structure of the entire 3D printed prosthetic socket 3 is included that, in a directly proportional manner, depends on at least one of data from a set including weight, patient's degree of activity, length of the residual limb, length of the prosthesis 6, size of the prosthetic foot 8, and angle between the axis of the limb and the axis of the prosthesis 6. When automatically determining the bulk density, the width of the walls, the bulk density of the reinforcements, etc., are selected. Furthermore, in this step, the type of the prosthetic socket 3 is selected, in case of an amputation below the knee of PTB, TSB, KBM, hybrid amputation type, or amputation above the knee of the prosthetic socket 3 type with support on the ischium or the prosthetic socket 3 type where the ischium is buried, in accordance with the performed modification of the area of the limb. In a preferred embodiment, this step also includes determining the shape of the 3D printed distal end of the prosthetic socket 3, which is subsequently used during the manufacture of the standard socket for capturing the axial location of the prosthetic socket 3 and axial position of the linking adapter of the socket 4. In a preferred embodiment, as shown in FIG. 9, this step further includes selecting the type of the suspension, namely lock, valve, string; and its positioning on the structural design of the 3D printed prosthetic socket 3. This step also includes positioning the linking part of the liner 10, positioning the linking adapter of the socket 4, and modifying the structural design of the 3D printed prosthetic socket 3, namely determining the location of the flexible region, changing the shape of the region, elements, and their density. The structural design of the 3D printed prosthetic socket 3 further includes a step of spatially arranging the digital representation of the area of the healthy limb relative to the digital representation of the modified area of the residual limb based on the axis of the limb and the axis of the prosthesis 6.

The bulk density of the structure of the distal end of the 3D printed prosthetic socket 3 means the density of representation of the reinforcing structures in the volume of the distal end, wherein the reinforcing structures do not fill the entire volume of the distal end, and therefore, the distal end comprises several cavities. In the case of a higher bulk density of the structure of the distal end, thanks to the increased number of the reinforcing structures, the distal end of the prosthetic socket 3 is reinforced, and the volume representation of the cavities at the distal end of the prosthetic socket 3 is simultaneously decreased. As the bulk density of the structure decreases, the proportion of the reinforcing structures decreases and the proportion of the cavities increases, thereby reducing the strength of the distal end and, simultaneously, reducing the amount of material needed to make the distal end of the prosthetic socket 3, thereby reducing its weight.

The step of virtually spatially arranging the prosthetic socket 3 and prosthetic parts, which is shown in FIGS. 10-22, includes mutually spatially arranging the model of the modified residual limb or, based on the area of the modified residual limb, the created shell of the prosthetic socket 3 and the models of the prosthetic parts. The prosthetic parts include the linking adapter of the socket 4; tube adapters 9; prosthetic foot 8, namely standard, dynamic, bionic; prosthetic joints 11; linking parts 10, namely lock, valve, string; knee joint 11. The selection of the prosthetic parts is performed based on the information about the patient and dimensional parameters of the residual limb. In another exemplary embodiment, the system offers only prosthetic parts compatible with the preceding selection of the parameters and parts. Furthermore, in this step, the shell is spatially arranged for the optimal load transfer from the axis of the limb to the axis of the prosthesis 6. The optimal load transfer from the axis of the limb to the axis of the prosthesis 6 is obtained by virtual translational or rotational movement of selected prosthetic parts and prosthetic socket 3. In the first exemplary embodiment of the virtual axial adjustment of the prosthesis 6 for the structural design of the 3D printed or standard prosthetic socket 3 with the 3D printed distal end, the alteration is implemented by both automatically mutually spatially arranging the prosthesis 6 and altering the mutual initial spatial arrangement of the prosthesis 6 by the user. In another exemplary embodiment of the virtual axial adjustment of the prosthesis 6 for the structural design of the 3D printed or standard prosthetic socket 3 with the 3D printed distal end, the alteration is implemented only by automatically mutually spatially arranging the prosthesis 6. In an exemplary embodiment, in which the mutual spatial arrangement of the transtibial prosthesis 6 is automatic, the prosthetic socket 3 of the prosthesis 6 is adjusted to the desired height based on the inputted location of the centre of the patellar ligament, for example, 51 cm. The location of the centre of the patellar ligament is selected based on the height of the healthy limb such that the symmetry of the healthy limb with the prosthesis 6 is ensured. The axis of the prosthetic socket 3 is adjusted to the desired flexion value, for example, 5 degrees in the sagittal plane, and the desired adduction value, for example, 5 degrees in the frontal plane. The flexion and adduction values of the axis of the prosthetic socket 3 are selected with respect to a vertical, which is defined by the load point of the prosthetic socket 3, on which, in the sagittal plane, the reference point 1 of the prosthetic foot 8 lies, which is determined by the manufacturer of the prosthetic foot 8, for example, ⅓ of the length from the heel, and in the frontal plane, the vertical passes through the centre of the heel. The prosthetic foot 8 is set at the desired heel height, for example, 1 cm. The adapter 9 and other adapters between the prosthetic socket 3 and prosthetic foot 8 are then automatically positioned in the junction of the linking adapters of the socket 4 and the prosthetic foot 8 based on the loading conditions mentioned above. In an exemplary embodiment, in which the mutual spatial arrangement of the transfemoral prosthesis 6 is automatic, the prosthetic socket 3 of the prosthesis 6 is adjusted to the desired height based on the inputted location of the ischium, for example, 83 cm. The location of the ischium is selected based on the height of the healthy limb such that the symmetry of the healthy limb with the prosthesis 6 is ensured. The axis of the prosthetic socket 3 is adjusted to the desired flexion value, for example, 5 degrees in the sagittal plane, and the desired adduction value, for example, 5 degrees in the frontal plane. The flexion and adduction values of the axis of the prosthetic socket 3 are selected with regard to the vertical, which is defined using the load point of the prosthetic socket 3. On this vertical, in the sagittal plane, the reference point 1 of the prosthetic foot 8 lies, which is determined by the manufacturer of the prosthetic foot 8, for example, ⅓ of the length from the heel, and in the frontal plane, the vertical passes through the centre of the heel. The prosthetic foot 8 is set at the desired heel height, for example, 1 cm. On this vertical, in the sagittal plane, the reference point 1 of the prosthetic knee joint 11 lies, which is determined by the manufacturer of the prosthetic knee joint 11, for example, 0-5 mm behind the vertical, and in the frontal plane, the vertical passes through the centre of the prosthetic knee joint 11. The adapter 9 and other adapters between the prosthetic knee joint 11 and prosthetic foot 8 are then automatically positioned in the junction of the prosthetic knee joint 11 and the prosthetic foot 8 based on the loading conditions mentioned above. Alternatively, the virtual initial axial adjustment of the prosthesis 6 for the structural design of the 3D printed or standard prosthetic socket 3 with a 3D printed distal end is implemented with the help of the user only. Furthermore, the step includes altering the outer surface of the prosthetic socket 3 such that the surface of the prosthetic socket 3 optically corresponds with the amputated limb. Alternatively, the alteration of the outer surface of the prosthetic socket 3 is performed such that the surface of the prosthetic socket 3 represents the corresponding region of the healthy paired limb. In a preferred embodiment, this step also includes cosmetically altering the outer surface of the prosthetic socket 3, wherein the cosmetic alteration is an alteration of the colour of the outer surface of the prosthetic socket 3 and perforation of the surface with openings of the selected shape. Furthermore, this step may include creating a cover 5 of the prosthetic socket 3, which is positioned between the distal end of the prosthetic socket 3 and foot 8. In an exemplary embodiment, the cover 5 may be of the PUR type, which is a foam cover requiring grinding into the desired shape manually or by CNC machining. In an alternative embodiment, the cover 5 may be of the 3DP type, which is a cover designed in CAD software or in the interactive configurator and subsequently printed on a 3D printer.

The step of the resulting summary of the design information includes an overview of the inputted parameters, including the residual limb, and information about the type, suspension, and embodiment of the prosthetic socket 3. Furthermore, the step comprises a list of the selected prosthetic parts and a list of the cosmetic alterations. In a preferred embodiment, this step further comprises a report containing the technical parameters, configuration, and material of the prosthesis 6. The resulting summary of the design information of the prosthesis 6 is shown in FIG. 23.

In the first exemplary embodiment, the approval of the design of the 3D printed or standard prosthetic socket 3 with the 3D printed distal end or the cover 5 includes both sending the printing data to the 3D printer and, simultaneously, creating an order form with a list of the selected components. In another exemplary embodiment, the approval of the design of the prosthetic socket 3 or the cover 5 includes sending the printing data, or data for the CNC machining, and creating an order form with a list of the selected components. In an alternative embodiment, the interactive configurator allows the transfer of certain parameters from the configuration to the calculation algorithm that performs a detailed calculation of the manufacturing data and then sends them to the manufacturing device. An advantage of this embodiment is the protection of the user and the protection of the calculation know-how. Alternatively, the data may not be connected to the 3D printer directly, instead, they may be sent to a contractual manufacturer, who will ensure individual processing of the data for their 3D printer.

LIST OF REFERENCE NUMBERS

1—Reference point
2—Zone
3—Prosthetic socket
4—Linking adapter of the socket
5—Cover
6—Prosthesis
7—Digital surface of the residual limb
8—Prosthetic foot
9—Tube adapter
10—Linking part of the liner
11—Prosthetic knee joint

What is claimed is:

1. A process of designing and manufacturing a 3D printed prosthetic socket comprising steps of:
   a) obtaining physical data about a patient with a residual limb, including at least one physical datum from a set comprising at least weight, degree of activity, geometry of axis of the residual limb, dimensional parameters of the residual limb, and dimensional parameters of the other limb,
   b) obtaining or creating a digital representation of a modified area of the residual limb,
   c) creating a structural design of the 3D printed prosthetic socket based on the obtained physical data about the patient, and/or based on the digital representation of the modified area of the residual limb,
   d) sending the data about the structural design of the prosthetic socket to the 3D printer,
   e) making the prosthetic socket using 3D printing,
   wherein the step of creating the structural design of the 3D printed prosthetic socket comprises a step of:
   determining the bulk density of the structure of the 3D printed prosthetic socket between a shaped area for positioning a linking part of the liner and a distal planar area for mounting a linking adapter of the socket directly proportional to at least one of the data from a set including at least weight, degree of activity of the patient, length of the residual limb, length of the prosthesis, size of the prosthetic foot, and angle between the axis of the limb and the axis of the prosthesis.

2. The process of designing and manufacturing the prosthetic socket of claim 1, wherein obtaining the physical data about the patient with the residual limb comprises a step of measuring the circumference of the residual limb in at least two anticoincident planes perpendicular to the axis of the limb, and their mutual distance, and their distance from a reference anatomical point of the residual limb.

3. The process of designing and manufacturing the prosthetic socket of claim 1, wherein the step of obtaining the digital representation of the modified area of the residual limb comprises a step of measuring the circumference of the residual limb in at least two anticoincident planes perpendicular to the axis of the limb, and their mutual distance, and their distance from the reference anatomical point of the residual limb, and a step of digitising the outer area of the residual limb based on the measured data.

4. The process of designing and manufacturing the prosthetic socket of claim 1, wherein the step of obtaining the digital representation of the modified area of the residual limb comprises a step of making a physical model of the residual limb, a step of modifying the outer area of the physical model of the residual limb, and a step of digitising the outer area of the modified physical model of the residual limb.

5. The process of designing and manufacturing the prosthetic socket of claim 1, wherein the step of obtaining the digital representation of the modified area of the residual limb comprises a step of digitising the inner area of the existing prosthetic socket or making the physical model of the residual limb from the existing prosthetic socket, and a step of digitising the outer area of the modified physical model of the residual limb.

6. The process of designing and manufacturing the prosthetic socket of claim 1, wherein the step of obtaining the digital representation of the modified area of the residual limb includes transforming the obtained data into a polygonal network of definition points of a density of at least 10 points per $cm^2$.

7. The process of designing and manufacturing the prosthetic socket of claim 1, wherein the structural design of the prosthetic socket comprises a step of obtaining a digital representation of the area of the healthy limb and a step of spatial arrangement of the digital representation of the area of the healthy limb relative to the digital representation of the modified area of the residual limb depending on the axis of the limb and the axis of the prosthesis.

* * * * *